(12) United States Patent
Grimard

(10) Patent No.: US 8,460,241 B2
(45) Date of Patent: Jun. 11, 2013

(54) NEEDLE PROTECTION ASSEMBLY WITH LOCKING ELEMENT

(75) Inventor: Jean-Pierre Grimard, Vif (FR)

(73) Assignee: Becton Dickinson France, Le Pont de Claix (FR)

( * ) Notice: Subject to any disclaimer, the term of this patent is extended or adjusted under 35 U.S.C. 154(b) by 11 days.

(21) Appl. No.: 12/937,672

(22) PCT Filed: Apr. 14, 2009

(86) PCT No.: PCT/IB2009/005474
§ 371 (c)(1),
(2), (4) Date: Nov. 30, 2010

(87) PCT Pub. No.: WO2009/144546
PCT Pub. Date: Dec. 3, 2009

(65) Prior Publication Data
US 2011/0112486 A1    May 12, 2011

(30) Foreign Application Priority Data
Apr. 16, 2008   (FR) ...................................... 08 02104

(51) Int. Cl.
*A61M 5/00*   (2006.01)
*A61M 5/32*   (2006.01)
*A61M 5/178*  (2006.01)
*A61M 5/31*   (2006.01)

(52) U.S. Cl.
USPC ...... 604/110; 604/198; 604/163; 604/164.08; 604/242

(58) Field of Classification Search
USPC .................................. 604/242, 110, 192, 187
See application file for complete search history.

(56) References Cited

U.S. PATENT DOCUMENTS
2004/0102740 A1* 5/2004 Meloul .......................... 604/263
2008/0183137 A1* 7/2008 Barrelle et al. ............... 604/198

FOREIGN PATENT DOCUMENTS
DE   102004063603 A1   7/2006
WO   2006/072807 A1    7/2006

* cited by examiner

*Primary Examiner* — Bhisma Mehta
*Assistant Examiner* — Lauren M Peng
(74) *Attorney, Agent, or Firm* — The Webb Law Firm

(57) ABSTRACT

The application relates to a needle protection assembly (1) comprising a support (2), a needle shield (8), urging means (10) located between said support (2) and said needle shield (8), tending to displace said needle shield (8) distally over said needle (3), wherein the assembly comprises one abutment (5) provided on said support (2), receiving a locking element (10a), a part of said urging means being laterally movable with respect to said support (2) and forming part of said locking element (10a).

14 Claims, 4 Drawing Sheets

NEEDLE PROTECTION ASSEMBLY WITH LOCKING ELEMENT

Figure 1:
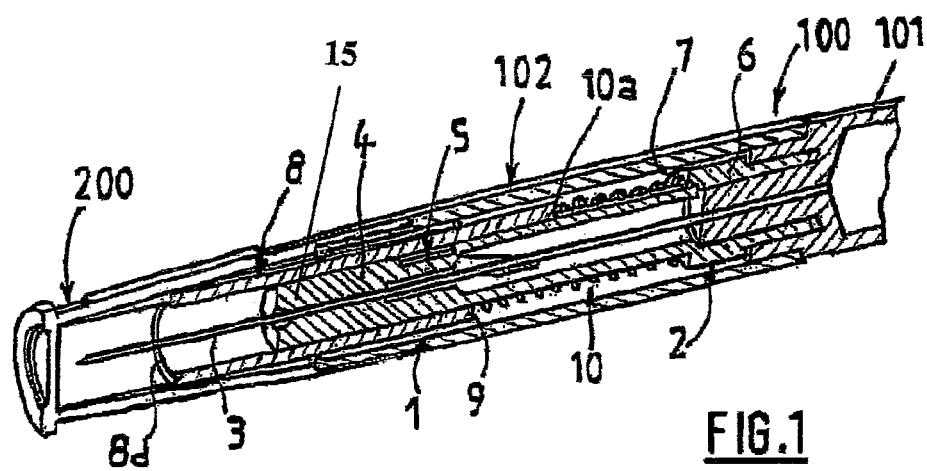

The present invention relates to a needle protection assembly that is to be connected to an injection device such as a syringe in view of completing an injection, said needle protection assembly being triggered after the injection in order to protect the user from accidental needle stick injuries and prevent needle re-use.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

In the medical field, it is usual to provide injection devices with needle protection systems in order to prevent the needle to be reached by the user or the patient before and/or after use of the injection device, in view of limiting accidental needle stick injuries. In addition, such needle protection systems also enable to prevent re-use of the injection devices.

Usually, the needle protection systems include a needle shield able to move distally over the needle once the injection is completed. The distal movement of the needle shield with respect to the needle is often triggered by a spring in an automatic way when the needle is withdrawn from the injection site. In general, the needle shield is then locked in its "after use" position thanks to a locking system, most of the time based on the cooperation of deflecting members located either on the needle hub and/or on the needle shield.

The document US2005/0113750 discloses such a needle protection system in which the locking system comprises a spring urging a needle shield toward its "after use" position and a deflecting leg provided on the needle shield, the deflecting leg being engaged into a groove provided on the needle hub in the "after use" position.

Nevertheless, the needle protection systems of the prior art have the drawback that, because of the energy necessary to deflect the deflecting members, the spring force must be high in order to displace the needle shield and overcome the deflecting members resistance. This has the consequence that, in storage position, before use, the high spring force of the compressed spring may deform the usual plastic parts forming the needle assembly and/or the injection device. This deformation may cause the needle protection system not to work properly at the time of use. This deformation may also cause wrong depth injection at the time of injection. Indeed, during the injection, the high spring force will push the needle shield against the skin, generating a push back force on the injection device proportional with the high force of the spring. This push back force will render difficult and unpredictable the accurate positioning of a constant pressure on the skin and make the injection operation more difficult to perform. In addition, springs with high force are more cumbersome, expensive and difficult to assemble than low duty spring. On the other side, low duty spring do not apply enough force to be able to overcome the deflecting members resistance and allow the needle protection system to work properly.

The document WO2006/072807 discloses a needle protection system in which the locking system comprises deflecting legs provided on the needle assembly and having to overcome friction forces with a needle shield in order to urge said needle shield toward its "after use" position. In the "after use" position, the deflecting legs are engaged into a groove provided on the needle shield.

The document US2004/0102740 discloses a needle protection system in which the locking system comprises a cap engaged into an abutment provided on the needle shield in the "after use" position of the device. When the cap is in the "after use" position, the needle may abut against the cap locked in the needle shield.

Moreover, some needle protection systems of the prior art necessitate a plurality of different parts, in particular parts forming the locking system, and are therefore difficult and long to manufacture.

There is therefore a need for a needle protection assembly, that would be easily triggered at the end of injection in order to avoid accidental needle stick for the user and re-use of the needle, and at the same time that would not be likely to cause the deformation of the plastic parts forming the needle assembly during storage, and that would be easy to assemble.

The present invention remedies to this problem by providing a needle protection assembly comprising a specific locking system so that the urging means, such as a spring, used to cause the distal movement of the protection at the end of injection is a low duty urging means that does not need to show a too high force.

The present invention relates to a needle protection assembly intended to protect the needle of a needle assembly, said needle protection assembly comprising at least:
   a support intended to be fixed relative to said needle,
   a needle shield intended to receive at least part of said needle and axially movable with respect to said support between an "in use" position in which said needle shield is intended to leave a portion of said needle uncovered, and an "after use" position in which said needle shield is intended to cover said needle,
   first urging means located between said support and said needle shield, and tending to displace said needle shield from said "in use" position to said "after use" position,
   a locking element located between said support and said needle shield and movable between at least a "free" position, in which said needle shield may be moved from its "in use" position to its "after use" position, and a "locking position", in which said locking element prevents said needle shield from moving back from its "after use" position to its "in use" position,
characterized in that said needle protection assembly further comprises
an abutment, located on said support, said abutment being designed for receiving said locking element and therefore defining said "locking" position of said locking element,
at least a part of said first urging means being laterally movable with respect to said support to cooperate with said abutment and forms at least part of said locking element.

In the needle protection assembly of the invention, the locking element is received in an abutment provided on the support when said locking element is in its "locking" position: as a consequence, the first urging means do not have to overcome any friction forces between said locking element and the needle shield when the needle shield is urged in its "after use" position. In the needle protection assembly of the invention, the urging means may therefore be dimensioned so that, in the storage position of the needle protection assembly, said urging means do not exert a high force on the various parts forming the needle protection assembly.

In an embodiment, said first urging means comprise at least a helical spring having several turns, said locking element comprises at least one turn of said helical spring.

In the needle protection assembly of the invention, the first urging means, for example a spring, combines two functions: it is used to cause the movement of the needle shield once the injection is completed and a specific part of this urging means forms a part of the locking system of the needle shield in its "after use" position. In this manner, the first urging means, in particular the spring, of the assembly of the invention does not need to overcome the friction force opposed by deflecting members of the locking systems of the prior art. Less force is required from the first urging means, such as the spring, of the needle protection assembly of the invention. In consequence, the first urging means of the needle protection assembly of the invention, even in the storage position, does not exert a high force on the plastic parts forming the assembly. The risks of deformation of these plastic parts are therefore limited with the needle protection assembly of the invention. In addition, as first urging means, a spring, weaker than the springs used in the devices of the prior art, may be used in the needle protection assembly of the invention.

Moreover, in the assembly of the invention, fewer parts are necessary since the urging means forms itself part of the locking system. The needle protection assembly of the invention is therefore easier to manufacture than assemblies of the prior art. The needle protection assembly of the invention, because it requires less manufacturing parts, is also environment friendly.

In an embodiment of the invention, the needle protection assembly further comprises second urging means tending to urge said locking element toward its locking position.

In an embodiment of the invention, said second urging means comprise a sloping surface.

Said sloping surface may be located on said needle shield, at least one end of said first urging means bearing on said sloping surface.

In an embodiment of the invention, the distal end of said first urging means is bearing on said sloping surface.

In an embodiment of the invention, said needle shield comprises at least one first part and one second part, said first part being intended to cover the needle in the "after use" position of the needle shield, said second part being provided with said sloping surface.

In an embodiment of the invention, said support comprises an inner core located in the needle shield, said inner core comprising on its external wall said abutment.

In an embodiment of the invention, said support comprises an outer sleeve located around said needle shield, said outer sleeve comprising on its inner wall said abutment.

In an embodiment of the invention, said needle shield is axially movable with respect to said support between a "before use" position, in which said needle shield covers at least part of the needle, and said "in use" position.

In an embodiment of the invention, the needle protection assembly comprises a cam, located on said needle shield or on said support, and a peg, respectively located on said support or on said shield, said cam and said peg being designed so as to cooperate together for defining at least one of said "in use" position and/or said "before use" position of the needle shield.

In an embodiment of the invention, part of said needle shield is received within part of said support.

In an embodiment of the invention, said abutment comprises at least one recess.

Another aspect of the invention is a needle assembly comprising at least a needle hub provided with a needle wherein it further comprises a needle protection assembly as described above. In an embodiment of the invention, said support comprises said needle hub.

Another aspect of the invention is an injection device comprising at least a needle assembly and a reservoir, wherein it further comprises a needle protection assembly as described above.

Figure 2:
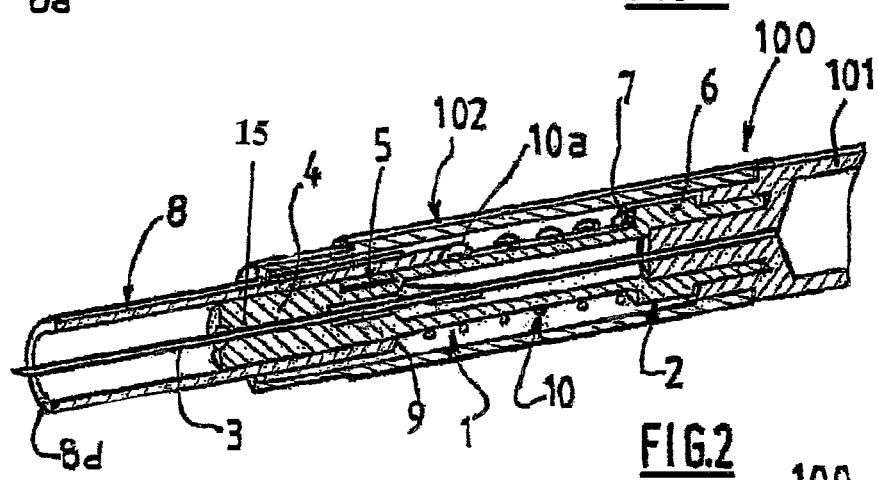
Figure 3:
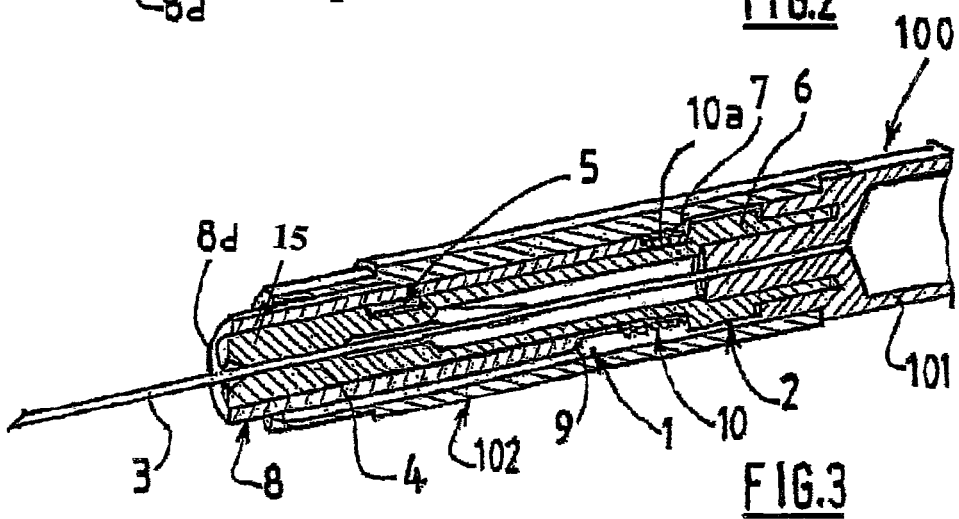
Figure 4:
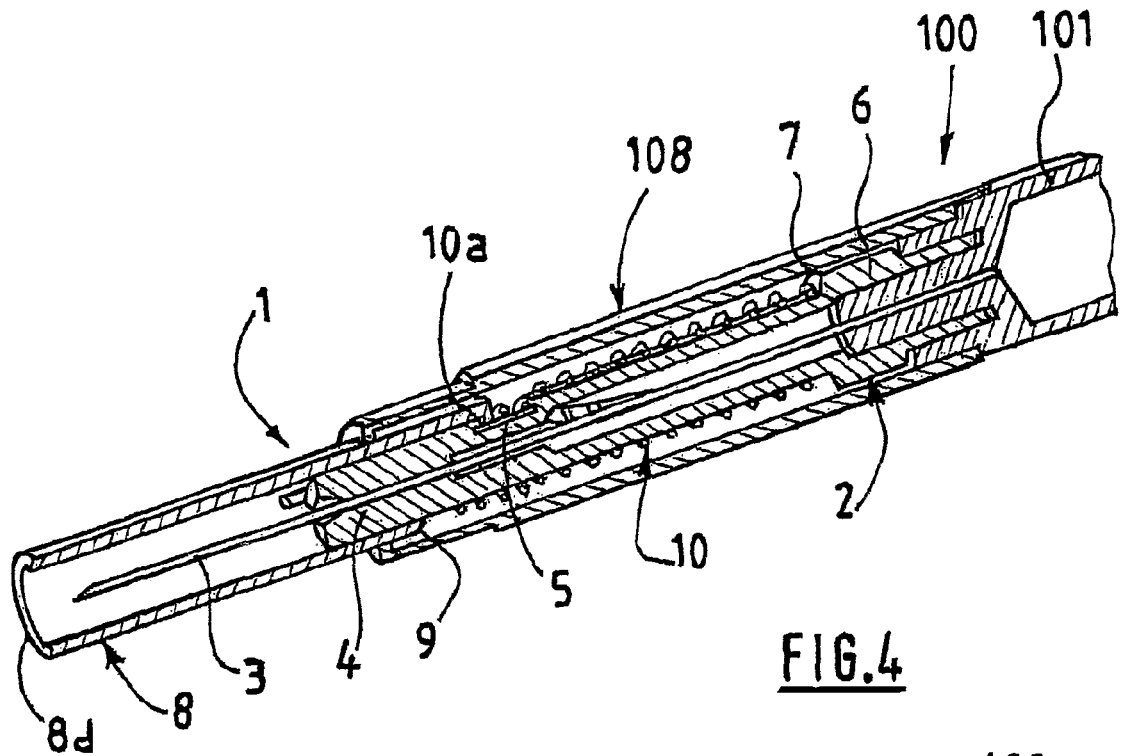
Figure 5:
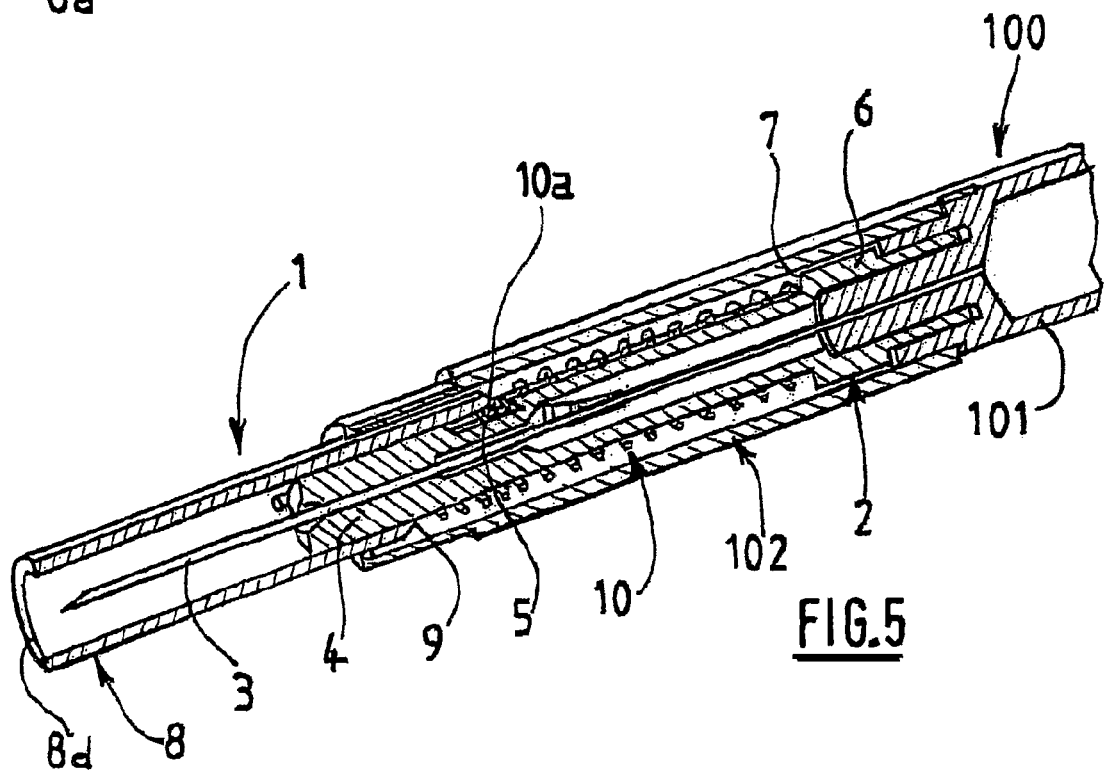
Figure 7:
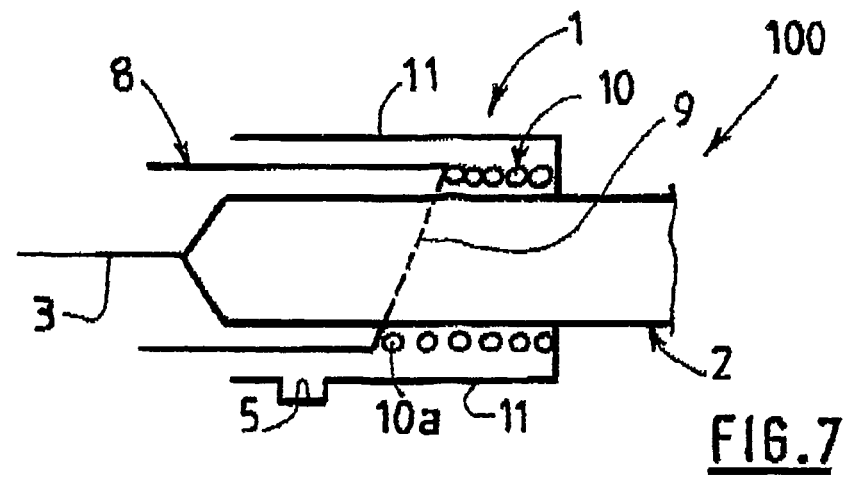
Figure 8:
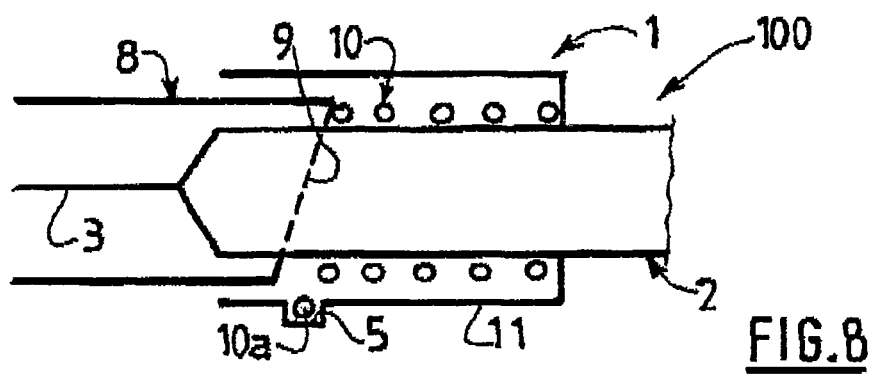

The needle protection assembly of the invention will now be further described in reference to the following description and attached drawings in which:

FIG. 1 is a cross section view of an injection device comprising a needle protection assembly according to the invention, in a "storage" position, said injection device being provided with a protection cap, FIG. 2 is a cross section view of the injection device of FIG. 1, in a "before use" position, once the protection cap has been removed, FIG. 3 is a cross section view of the injection device of FIG. 1 during injection, namely in an "in use" position, FIG. 4 is a cross section view of the injection device of FIG. 1 in an "after use" position, right at the end of the injection, FIG. 5 is a cross section view of the injection device of FIG. 1 in an "after use" position, once one has tried to push backwards the needle shield, FIGS. 6A to 6D are partial views of the needle protection assembly of the injection device of FIGS. 1-5 showing the peg position in the cam, respectively in the following positions: "storage", "before use", "in use" and "after use", FIGS. 7 and 8 are schematic views of an alternative of the needle protection assembly of the invention respectively in the "in use" position and in the "after use" position.

In reference to FIG. 1 is shown a needle protection assembly 1 according to the invention, mounted on an injection device 100 (partially shown). The injection device 100 is in a "storage" position and its distal end is covered with a protection cap 200. The needle protection assembly 1 of the invention comprises a support 2 that bears a needle 3. The support 2 comprises an inner core 4, said inner core 4 comprising on its outer wall an abutment 5. In one embodiment, a portion of support 2 forms a needle hub 15. For example, a portion of inner core 4 of support 2 forms a needle hub 15. The support 2 also comprises a proximal part 6 of outer diameter larger than the outer diameter of the inner core 4 and forming with respect to said inner core 4 a rim 7. As shown on FIGS. 6A to 6D, the outer wall of the support 2, for example the outer wall of the inner core 4, is provided with a longitudinal cam 4a having the global shape of a V, the function of which will be explained later.

The needle protection assembly 1 of FIG. 1 also comprises a needle shield 8 receiving at least partially said support 2 and in particular said inner core 4 of said support 2. The needle shield 8 has a substantially tubular shape and is provided at its proximal end with a sloping surface 9, the function of which will be explained later. As shown on FIGS. 6A to 6D, the needle shield 8 is provided with a peg 8a able to cooperate with the cam 4a so as to define respectively a "before use", a "in use" and a "after use" positions of the needle shield 8. These positions are described hereafter. For sake of clarity, the needle shield 8 is not shown on FIGS. 6A-6B: only the peg 8a, which is part of said needle shield 8, is shown on these figures.

As will appear clearly from the description of FIGS. 2-5, the needle shield 8 is axially movable with respect to the support 2 between a "before use" position, in which said needle shield 8 covers at least part of the needle 3, as shown on FIG. 2, an "in use" position in which said needle shield 8 leaves a portion of said needle 3 visible, as shown on FIG. 3, and an "after use" position in which said needle shield 8 covers said needle 3, as shown on FIGS. 4 and 5.

The needle protection assembly 1 of FIG. 1 further comprises a helical spring 10, acting as first urging means and located between the support 2 and the needle shield 8. On the example shown on FIG. 1, the proximal end of the spring 10 bears on the rim 7 and its distal end bears on the sloping surface 9 of the needle shield 8. In the "storage" position shown on FIG. 1, the helical spring 10 is in a partially expanded state.

The helical spring 10 comprises several turns, its very distal turn 10a bearing on said sloping surface 9 of said needle shield 8.

The injection device 100 of FIG. 1 also comprises a barrel 101 (partially shown) intended to receive a product to be injected and an outer housing 102 receiving said barrel 101 and the needle protection assembly 1.

The operation of the needle protection assembly 1 and of the injection device 100 will now be explained in reference to FIGS. 1-5.

On FIG. 1, the injection device 100 is in a "storage" position. The distal end of the injection device 100 is covered with a protection cap 200 in order to avoid accidental needle stick injury for any person having to handle the injection device 100. As shown on FIG. 6A, the peg 8a is in a free position in a first branch of the V-shaped cam 4a.

In order to proceed with the injection, the user removes the protection cap 200 as shown on FIG. 2. In this "before use" position shown on FIG. 2, the needle shield 8 covers part of the needle 3. In an example not shown, the needle shield 8 could cover the entire needle 3 so as to prevent any accidental needle stick injury in this position.

Figure 6A:
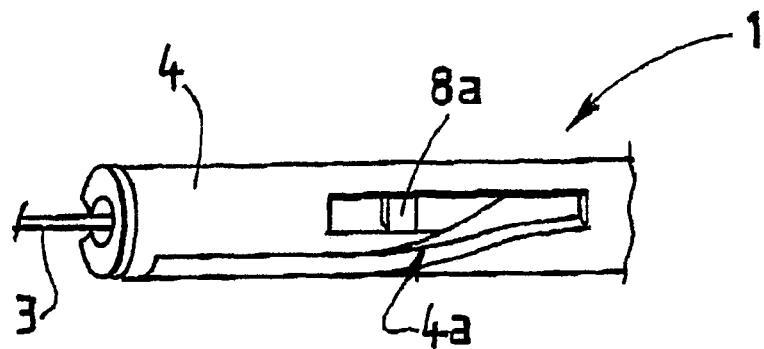
Figure 6B:
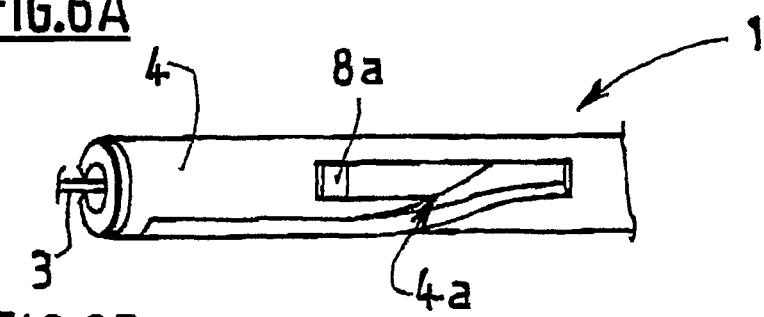
Figure 6C:
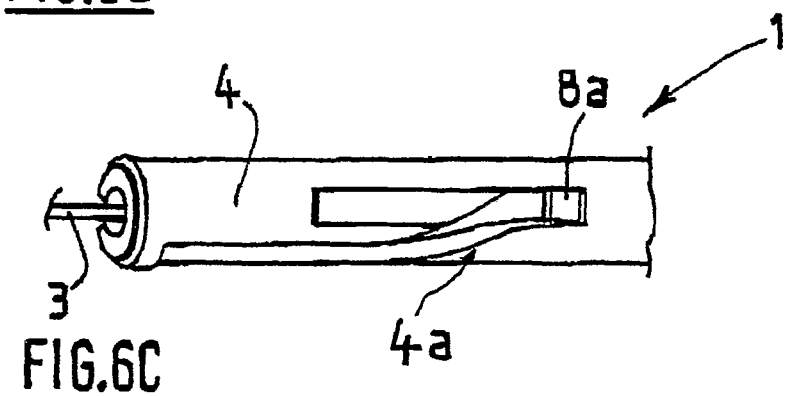
Figure 6D:
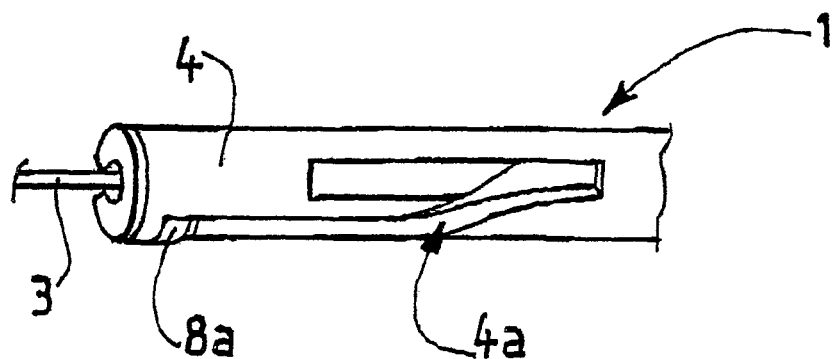

In the position shown on FIG. 2, the helical spring 10 is in a slightly less compressed state than in FIG. 1, namely in a partially expanded state and, as shown on FIG. 6B, the peg 8a abuts in the free extremity of the first branch of the cam 4a.

The user then applies the injection device 100 on the skin of a patient (not shown), inserts the needle 3 into the injection site until the distal end 8d of the needle shield 8 comes in contact with the skin. In order to fully insert the needle 3 in the site of injection, the user then exerts a distal pressure on the injection device 100, this having as a consequence to cause the distal movement of the support 2 with respect to the needle shield 8, as shown on FIG. 3, said needle shield 8 being blocked against the skin of the patient (not shown). During the distal movement of the support 2, the rim 7 has come closer to the sloping surface 9 of the needle shield 8 and the helical spring 10 is now in a compressed state, as shown on FIG. 3. As shown on FIG. 6C, the peg 8a is then in abutment on the junction point of the two branches forming the V-shaped cam 4a. The needle shield 8 is in its "in use" position. The user may then realise the injection of the product to be injected.

Once the injection step (not shown) is completed, the user removes the injection device 100 from the injection site and the needle shield 8 is no more blocked by the skin of the patient. The helical spring 10 is therefore free to return to its expanded state and it causes the distal movement of the needle shield 8 with respect to the support 2 as shown on FIG. 4. The needle shield 8 deploys and covers the needle 3, thereby preventing any accidental needle stick injury for the user and any re-use of the injection device 100.

While expanding, the very distal turn 10a of the helical spring 10, that bears on the sloping surface 9 of the needle shield 8, has come in regard with the abutment 5 provided on the outer wall of the inner core 4 of the support 2. The sloping surface 9, acting as second urging means, has urged the very distal turn 10a of the helical spring 10 into said abutment 5. As shown on FIG. 4, the very distal turn 10a of the helical spring 10 is now received in the abutment 5 of the support 2. As shown on FIG. 6D, the peg 8a abuts against the free extremity of the second branch of the V-shaped cam 4a.

As will appear from FIG. 5, the very distal turn 10a of the helical spring 10 acts as a locking element capable of having a free position, shown on FIGS. 2 and 3, in which it allows the movement of the needle shield 8 from its "in use" position to its "after use" position, and a locking position, shown on FIGS. 4 and 5, in which it prevents the needle shield 8 to come back from its "after use" position to its "in use" position.

Actually, on FIG. 5 is shown the injection device 100 once one has tried to push backwards, namely in the proximal direction, the needle shield 8. In consequence to this proximal pressure exerted on the distal end 8d of the needle shield 8, the very distal turn 10a of the helical spring 10 becomes entangled together with the adjacent turns of the helical spring 10 within the abutment 5 and the needle shield 8 is blocked in the proximal direction and can not be moved back to an "in use" position.

In the needle protection assembly 1 and the injection device 100 of the invention, because the locking element 10a is under the form of a turn of the helical spring 10, the helical spring 10 does not have to overcome the friction force of deflecting members forming the usual locking systems of the needle protection systems of the prior art. For this reason, the force of the helical spring 10 of the needle protection assembly 1 and the injection device 100 of the invention does not need to be high. In consequence, when the needle protection assembly 1 and the injection device 100 of the invention are in a "storage" position, as shown on FIG. 1, the force exerted by the helical spring 10 on the different parts forming the needle protection assembly 1 and/or the injection device 100 is not high and does not deform said parts. The helical spring 10 is not cumbersome and the needle protection assembly 1 and/or the injection device 100 can have moderate size. In addition, the helical spring 10 is easy to assemble because it requires less pressure to be compressed than a high force spring.

As previously described, the needle protection assembly 1 of FIGS. 1 to 5 has four positions:
- a "storage" position in which the needle 3 is protected by the protection cap 200,
- a "before use" position after retrieval of the protection cap 200 and before proper use of the injection device 100, in this "before use" position the needle 3 is at least partly covered by the needle shield 8,
- a "in use" position during which the injection device 100 is applied against the injection site, the needle 3 is inserted in the injection site and is not covered by the needle shield 8,
- a "after use" position after withdrawal of the needle from the injection site, in this "after use" position, the needle shield 8 covers the needle 3.

In an embodiment not shown, the needle shield may be provided with a cam able to receive therein a peg located on the outer wall of the support, said cam and said peg being able to cooperate so as to define respectively the "before use", the "in use" and the "after use" positions of the needle shield.

On FIGS. 7 and 8 is shown schematically an alternative of the needle protection assembly 1 of the invention respectively in the "in use" position and in the "after use" position. The references designating the same elements as in FIGS. 1-5 have been maintained.

On FIG. 7 is shown a needle protection assembly 1 according to the invention comprising a support 2, a needle shield 8 and a spring 10 located between the support 2 and the needle shield 8. The support 2 further comprises an outer sleeve 11 located around the needle shield 8, said outer sleeve 11 comprising on its inner wall a abutment 5.

In the "in use" position of the needle shield 8, as shown on FIG. 7, the locking element, under the form of the very distal turn 10a of the spring 10, bears on the sloping surface 9 of the needle shield 8 and is therefore in its "free position", allowing the movement of the needle shield 8 from the in "use position" to the "after use" position, shown on FIG. 8.

Once the user has removed the injection device (not shown) from the skin of the patient, the spring 10, which was in its compressed state on FIG. 7, expands in the distal direction, causing the distal movement of the needle shield 8 which deploys over the needle 3. Stops and abutment (not shown) located on the inner wall of the outer sleeve 11 and on the outer wall of the needle shield 8 prevent the disassembling of the needle shield 8 from the outer sleeve 11. At the same time, the very distal turn 10a of the helical spring 10 has come in regard with the abutment 5 located on the inner wall of the outer sleeve 11 of the support 2. The sloping surface 9 has then urged the very distal turn 10a of the helical spring 10 into the abutment 5. As already seen for the embodiment of FIGS. 1-5, the very distal turn 10a of the helical spring 10 becomes entangled with its adjacent turns within the abutment 5 and the needle shield 8 becomes blocked in translation in the proximal direction and can not be moved back toward an "in use" position.

Before its "in use" position, this needle protection assembly 1 may be:
- in a "before use" position different from the "after use" position and in which the needle 3. is partly covered by the needle shield 8, in this case the needle protection assembly 1 is a three positions one, or
- in a "before use" position similar to the "after use" position in which the needle is covered by the needle shield 8, in this case the needle protection assembly 1 is a two positions one.

Additionally, prior the use of the injection device 100, the needle 3 may be protected by a cap (as for FIGS. 1 to 5) that may force the needle shield 8 to be in an additional "storage" position giving respectively a four or three positions needle protection assembly 1.

The invention claimed is:

1. A needle protection assembly adapted to protect a needle, said needle protection assembly comprising:
   a support adapted to be fixed relative to said needle,
   a needle shield adapted to receive at least part of said needle and axially movable with respect to said support between an in use position in which said needle shield leaves a portion of said needle uncovered, and an after use position in which said needle shield covers said needle,
   first urging means located between said support and said needle shield and tending to displace said needle shield from said in use position to said after use position,
   a locking element located between said support and said needle shield and movable between at least a free position, in which said needle shield may be moved from said in use position to said after use position, and a locking position, in which said locking element prevents said needle shield from moving back from said after use position to said in use position, and
   an abutment, located on said support, said abutment adapted to receive said locking element and therefore defining said locking position of said locking element,
   wherein at least a part of said first urging means is laterally movable with respect to said support to cooperate with said abutment and forms at least part of said locking element, and
   wherein said first urging means comprises at least a helical spring having a plurality of turns, and said locking element comprises at least one turn of said helical spring.

2. The needle protection assembly according to claim 1, further comprising a second urging means tending to urge said locking element toward said locking position.

3. The needle protection assembly according to claim 2, wherein said second urging means comprises a sloping surface.

4. The needle protection assembly according to claim 3, wherein said sloping surface is located on said needle shield, at least one end of said first urging means bearing on said sloping surface.

5. The needle protection assembly according to claim 4, wherein the distal end of said first urging means is bearing on said sloping surface.

6. The needle protection assembly according to claim 3, wherein said needle shield comprises at least one first part and one second part, said first part being intended to cover the needle in the after use position of the needle shield, said second part being provided with said sloping surface.

7. The needle protection assembly according to claim 1, wherein said support comprises an inner core located in the needle shield, said inner core comprising on its external wall said abutment.

8. The needle protection assembly according to claim 1, wherein said support comprises an outer sleeve located around said needle shield, said outer sleeve comprising on its inner wall said abutment.

9. The needle protection assembly according to claim 1, wherein said needle shield is axially movable with respect to said support between a before use position, in which said needle shield covers at least part of the needle, and said in use position.

10. The needle protection assembly according to claim 9, further comprising a cam, located on said needle shield or on said support, and a peg, respectively located on said support or on said needle shield, said cam and said peg being designed so as to cooperate together for defining at least one of said in use position and/or said before use position of the needle shield.

11. The needle protection assembly according to claim 1, wherein part of said needle shield is received within part of said support.

12. The needle protection assembly according to claim 1, wherein said abutment comprises at least one recess.

13. The needle protection assembly according to claim 1, further comprising a needle hub provided with said needle.

14. The needle protection assembly according to claim 13, wherein said support comprises said needle hub.

* * * * *

UNITED STATES PATENT AND TRADEMARK OFFICE
CERTIFICATE OF CORRECTION

PATENT NO.         : 8,460,241 B2
APPLICATION NO.    : 12/937672
DATED              : June 11, 2013
INVENTOR(S)        : Jean-Pierre Grimard Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 54 days.

Signed and Sealed this
Eighth Day of September, 2015

Michelle K. Lee
*Director of the United States Patent and Trademark Office*